United States Patent [19]
Wallace

[11] Patent Number: 5,830,171
[45] Date of Patent: Nov. 3, 1998

[54] PUNCTAL OCCLUDER

[75] Inventor: Raymond G Wallace, Bartlett, Tenn.

[73] Assignee: Odyssey Medical, Inc., Memphis, Tenn.

[21] Appl. No.: 909,839

[22] Filed: Aug. 12, 1997

[51] Int. Cl.$^6$ .................................................. A61M 5/00
[52] U.S. Cl. .................................................. 604/8; 604/104
[58] Field of Search .................................. 604/8–10, 104, 604/285, 294

[56] References Cited

U.S. PATENT DOCUMENTS

| | | |
|---|---|---|
| 3,949,750 | 4/1976 | Freeman . |
| 4,660,546 | 4/1987 | Herrick et al. . |
| 4,915,684 | 4/1990 | MacKeen et al. . |
| 4,959,048 | 9/1990 | Seder et al. . |
| 5,049,142 | 9/1991 | Herrick et al. . |
| 5,053,030 | 10/1991 | Herrick et al. . |
| 5,163,959 | 11/1992 | Herrick ............................................ 2/2 |
| 5,171,270 | 12/1992 | Herrick ............................................ 2/2 |
| 5,334,137 | 8/1994 | Freeman . |
| 5,723,005 | 3/1998 | Herrick ........................................... 2/14 |

*Primary Examiner*—Aaron J. Lewis
*Assistant Examiner*—Ki Yong
*Attorney, Agent, or Firm*—Walker, McKenzie & Walker, P.C.

[57] ABSTRACT

A punctal occluder for blocking the flow of lacrimal fluid from the surface of an eye through a lacrimal punctum. The punctal occluder includes a shank having a distal end for insertion into the lacrimal punctum; and a distal flange attached to the distal end of the shank for insertion into the lacrimal punctum; the distal flange including a wing portion having a first position extending substantially along the shank for allowing easy insertion of the distal flange into the lacrimal punctum, and having a second position extending substantially outward from the shank for hindering unintentional removal of the distal flange from the lacrimal punctum.

6 Claims, 2 Drawing Sheets

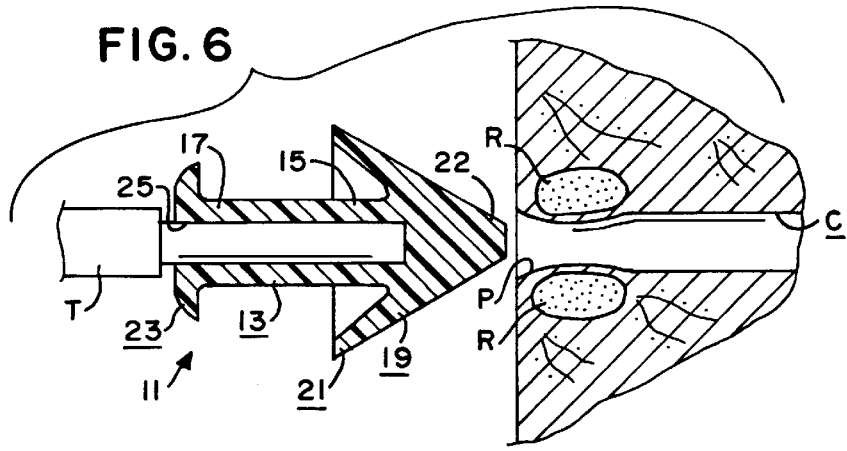
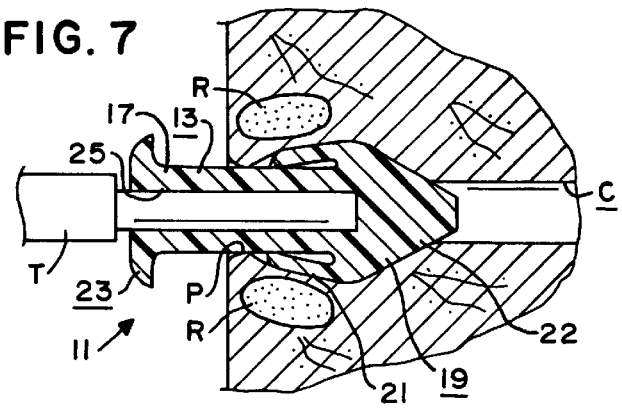
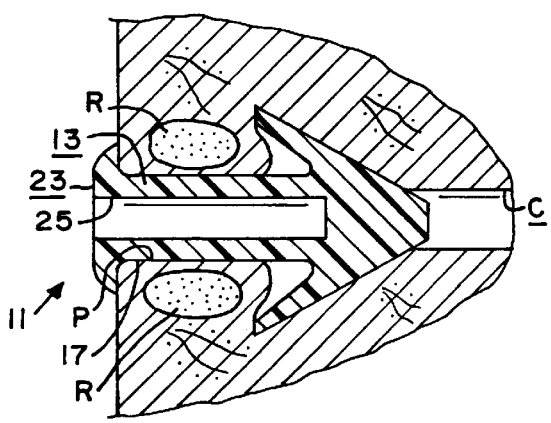
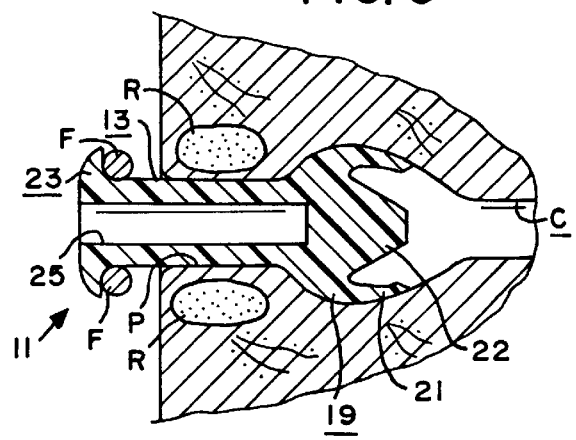

PUNCTAL OCCLUDER

CROSS-REFERENCE TO RELATED APPLICATIONS

Not applicable.

STATEMENT RE FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present invention relates, in general, to tear duct implants for insertion into and blocking one or more punctal openings of a person's eyes.

2. Information Disclosure Statement

Tears help to protect, lubricate, and cleanse the surface of the eye with every blink. However, many people do not consistently produce enough tears to perform all of these very necessary functions. The result is burning, stinging, scratchiness, and redness around the eyes. Fatigue usually results after only very short periods of reading and use of contact lenses can only make matters worse. With a lack of tear film on the surface of the eye, dry areas on the cornea begin to expand and contribute to the condition known as dry eye syndrome or keratoconjunctivitis sicca.

Many of these symptoms can cause severe medical problems and can even worsen in dry environments, with contact lenses, and with the aging process. Some medications can also exacerbate dry eyes by decreasing lacrimal gland secretion. In addition, dry eyes can be a symptom of other diseases and should be carefully diagnosed by physicians or professionals trained in the identification and treatment of dry eye syndrome.

Once the dry eye condition is confirmed, there are several recognized options for treatment. Many doctors start immediately with a topical therapy; however, moderate or severe cases generally dictate more aggressive strategies, such as punctal occlusion. Occlusion can be temporary, in the form of collagen plugs which dissolve in about a week after insertion, or more permanent (but reversible) with silicone plugs. There are two basic types of permanent strategies used today, intracanalicular plugs and punctal opening plugs.

Punctal plugs increase the tear level in the eye by restricting the outflow of tears. Increased tear level and the amount of time the tear is in contact with the eye improves the health and condition of the cornea.

Freeman, U.S. Pat. No. 3,949,750, issued Apr. 13, 1976, discloses a punctum plug having a solid cone shaped tip or barb portion, a disk or dome shaped head portion, and a cylindrical shaft or neck joining the barb and head portions.

Herrick et al., U.S. Pat. Nos. 4,660,546, issued Apr. 28, 1987, and 5,049,142, issued Sep. 17, 1991, and 5,053,030, issued Oct. 1, 1991, disclose intracanalicular implants having a shaft-like body for being fully inserted into a patient's canaliculus.

MacKeen et al., U.S. Pat. No. 4,915,684, issued Apr. 10, 1990, discloses a punctum plug having a cone or barbed shaped tip portions, a dome shaped head portion, and a cylindrical shaft or neck joining the tip and head portions. An aperture extends completely through the plug to allow lacrimal fluid to be modulated.

Seder et al., U.S. Pat. No. 4,959,048, issued Sep. 25, 1990, discloses a lacrimal duct occluder formed of a shaft having a low profile cap at one end and a rounded tip at the other end.

Freeman, U.S. Pat. No. 5,334,137, issued Aug. 2, 1994, discloses a punctum plug having a solid cone shaped tip or barb portion, a disk or dome shaped head portion, and a cylindrical shaft or neck joining the barb and head portions, the shaft having a conical portion adjacent the tip portion for being acted on the punctal ring to produce a resultant force vector directed toward the tip portion to facilitate retention of the punctum plug within the punctal opening.

Nothing in the known prior art discloses or suggests the present invention. More specifically, nothing in the known prior art discloses or suggests a punctal occluder including a shank having a distal end for insertion into a lacrimal punctum, and a distal flange attached to the distal end of the shank for insertion into the lacrimal punctum; the distal flange including a wing portion having a collapsed position for allowing easy insertion of the distal flange into the lacrimal punctum, and having an opened position for hindering unintentional removal of the distal flange from the lacrimal punctum.

BRIEF SUMMARY OF THE INVENTION

The present invention provides a punctal occluder or plug that can be easily inserted into and removed from a lacrimal punctum. A basic concept of the present invention is to provide punctal occluder including a shank and a distal flange with a wing portion having a collapsed position for allowing easy insertion of the distal flange into the lacrimal punctum, and having an opened position for hindering unintentional removal of the distal flange from the lacrimal punctum.

The punctal occluder of the present invention comprises, in general, a shank having a distal end for insertion into a lacrimal punctum, and a distal flange attached to the distal end of the shank for insertion into the lacrimal punctum; the distal flange including a wing portion having a collapsed position for allowing easy insertion of the distal flange into the lacrimal punctum, and having an opened position for hindering unintentional removal of the distal flange from the lacrimal punctum.

One object of the present invention is to provide a punctal occluder than can be very easily inserted into any punctal opening.

Another object of the present invention is to provide such a punctal occluder that, when inserted, springs open to fill a very wide range of punctal duct sizes.

Another object of the present invention is to provide such a punctal occluder that resists accidental removal from the punctum.

Another object of the present invention is to provide such a punctal occluder having a distal flange that reverses shape for quick and easy removal.

Another object of the present invention is to provide such a punctal occluder having a distal flange that naturally conforms to the shape of the surrounding punctal tissue.

Another object of the present invention is to provide such a punctal occluder that is very strong, yet soft and elastic.

Another object of the present invention is to provide such a punctal occluder that can be manufactured in only three sizes to fit virtually every punctal size and occlusive requirement, while simplifying size selection and lowering inventory cost requirements.

Another object of the present invention is to provide such a punctal occluder that is manufactured out of a soft implant material designed to match the feel and texture of the surrounding tissue, while maintaining strength for function.

BRIEF DESCRIPTION OF THE SEVERAL VIEWS OF THE DRAWINGS

FIG. 6 is a sectional view of the punctal occluder of the present invention similar to FIG. 3, but shown somewhat diagrammatically mounted on the distal end of an insertion tool just prior to insertion into the mouth of a lacrimal punctum.

FIG. 7 is a sectional view of the punctal occluder of the present invention similar to FIG. 3, but shown somewhat diagrammatically mounted on the distal end of an insertion tool and partially inserted into a lacrimal punctum.

FIG. 8 is a sectional view of the punctal occluder of the present invention similar to FIG. 3, but shown somewhat diagrammatically fully inserted into a lacrimal punctum.

FIG. 9 is a sectional view of the punctal occluder of the present invention similar to FIG. 3, but shown somewhat diagrammatically grasped by a removal tool and partially removed from the lacrimal punctum.

DETAILED DESCRIPTION OF THE INVENTION

Figure 1:
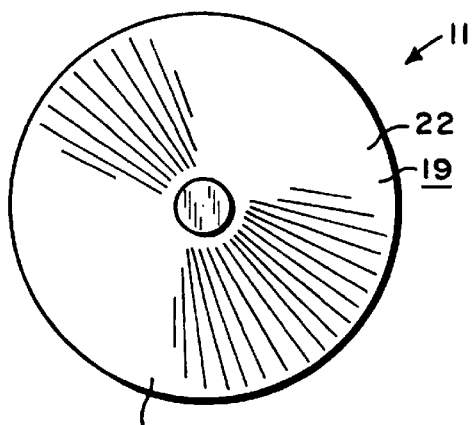
FIG. 1 is a top plan view of the punctal occluder of the present invention.
Figure 2:
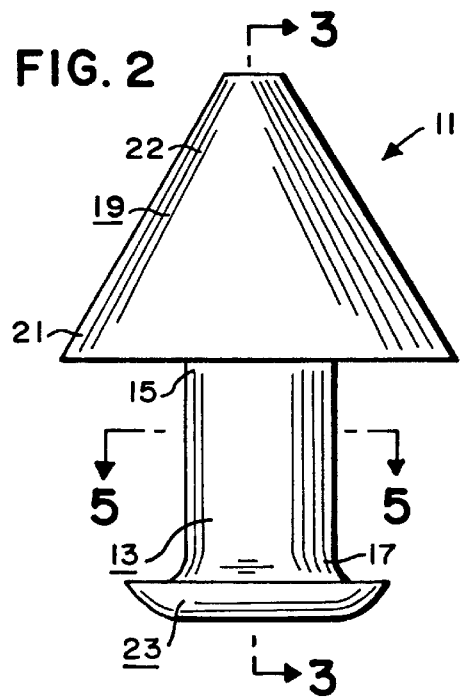
FIG. 2 is a side elevational view of the punctal occluder of the present invention, all other sides being mirror images thereof.
Figure 3:
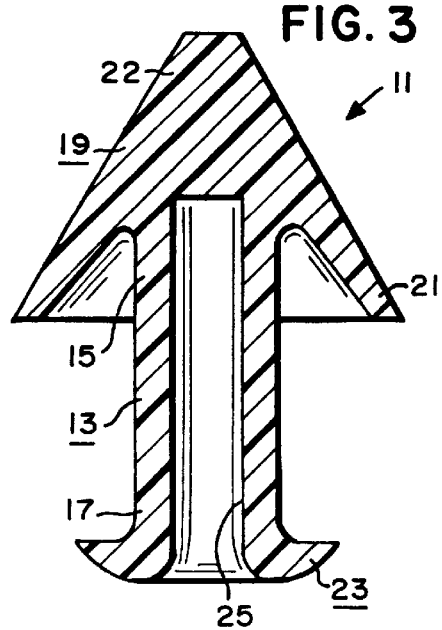
FIG. 3 is a sectional view as taken on line 3—3 of FIG. 2.
Figure 4:
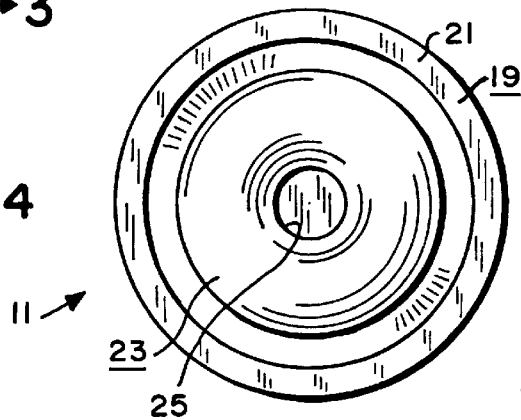
FIG. 4 is a bottom plan view of the punctal occluder of the present invention.
Figure 5:
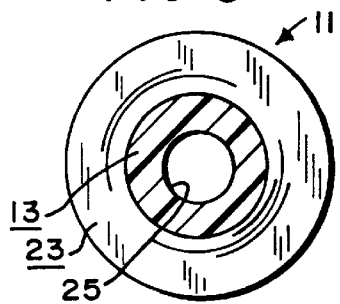
FIG. 5 is a sectional view as taken on line 5—5 of FIG. 2.

A preferred embodiment of the punctal occluder of the present invention is shown in FIGS. 1–9, and identified by the numeral 11. The punctal occluder 11 is for inserting into a patient's lacriminal punctum P and lacrimal canaliculus C (see, in general, FIGS. 6–9) to block the flow of lacrimal fluid from the surface of an eye through the lacrimal punctum P.

The punctal occluder 11 includes a shank 13 having a distal end 15 for insertion through the lacrimal punctum P and into the lacrimal canaliculus C, and having a proximal end 17. The shank 13 preferably has a circular cross sectional area as clearly shown in FIG. 5.

The punctal occluder 11 includes a distal flange 19 attached to the distal end 15 of the shank 13 for insertion through the lacrimal punctum P, past the punctal ring R (i.e., the sphincter or ring of muscle or fibroelastic tissue adjacent the lacrimal punctum P), and into the lacrimal canaliculus C. The distal flange 19 includes a wing portion 21 having a first or collapsed position as clearly shown in FIG. 7 for allowing easy insertion of the distal flange 19 through the lacrimal punctum P, past the punctal ring R, and into the lacrimal canaliculus C, and having a second or opened or expanded position as clearly shown in FIG. 8 for hindering unintentional removal of the distal flange 19 from the lacrimal canaliculus C and lacrimal punctum P. The wing portion 21 of the distal flange 19 preferably has a third or reversed or "inside-out" position as clearly shown in FIG. 9 for allowing easy removal of the distal flange 19 from the lacrimal canaliculus C and lacrimal punctum P. The wing portion 21 of the distal flange 19 is preferably normally urged to the second or opened position. The distal flange 19 preferably has a truncated cone shaped nose or distal end portion 22 and the wing portion 21 preferably forms an extension of the outer wall of the truncated cone shaped nose portion 22 as clearly shown in FIG. 3. The wing portion 21 is substantially soft and flexible to allow it to be easily urged to the first or collapsed position as shown in FIG. 7 as the distal flange 19 is pushed through the lacrimal punctum P and punctal ring R, and to allow it to be easily urged to the third or reversed, "inside-out" position as shown in FIG. 9 as the distal flange 19 is pulled out of the lacrimal canaliculus C, past the punctal ring R and lacrimal punctum P. However, the wing portion 21 preferably has sufficient "memory" so that after it is pushed through the lacrimal punctum P and punctal ring R, it will expand or open from the first position back toward the second position to fully block the lacrimal canaliculus C, as illustrated in FIGS. 7 and 8. The wing portion 21 may be formed by a plurality of individual wing elements attached to and spaced about the proximal end of the nose portion 22. Preferably, however, the wing portion 21 consist of a thin membrane of a soft, flexible material extending from the proximal end of the nose portion 22 as a continuous, one-piece ring with the outer surface thereof extending parallel and aligned with the outer surface of the nose portion 22 when the wing portion 21 is in the second or normal position as clearly shown in FIG. 8, whereby the outer surfaces of the nose portion 22 and wing portion 21 coact to form a continuous cone shape when the wing portion 21 is in the second or normal position as clearly shown in FIG. 8. The shape and function of the preferred distal flange 19 is thus somewhat suggestive of a typical umbrella, i.e., somewhat suggesting a closed umbrella when the wing portion 21 is in the first or closed portion, somewhat suggesting an opened umbrella when the wing portion 21 is in the second or opened position, and somewhat suggesting a wind-blown, inside-out umbrella when the wing portion 21 is in the third or reversed position.

The punctal occluder 11 preferably includes a proximal flange or dome 23 attached to the proximal end 17 of the shank 13 for abutting the mouth of the lacrimal punctum P when the punctal occluder 11 is fully inserted into the lacrimal canaliculus C and lacrimal punctum P to prevent complete migration of the punctal occluder 11 into the lacrimal canaliculus C.

The punctal occluder 11 preferably has an aperture 25 extending through the proximal flange 23, through the shank 13, and into but not completely through the distal flange 19 for receiving the tip of an insertion tool T or other dispenser whereby the punctal occluder 11 can be held and inserted by such an insertion tool T or the like.

The punctal occluder 11 may be constructed in various manners and out of various materials as will now be apparent to those skilled in the art. At least the wing portion 21 of the distal flange 19 is constructed out of a material that is soft and flexible in its final state, such as silicone plastic, for allowing movement thereof from the opened position shown in FIG. 6 to the collapsed position shown in FIG. 7 when force is directed inwardly on the wing portion 21 (e.g., when the distal flange 19 is inserted into the lacrimal canaliculus C, through the lacrimal punctum P and past the punctal ring R), and from the opened position shown in FIG. 8 to the reversed position shown in FIG. 9 when force is directed on the wing portion 21 in a direction toward the distal end 15 of the shank 13 (e.g., when the distal flange 19 is withdrawn from the lacrimal canaliculus C, past the lacrimal punctum P and punctal ring R). Such material preferably has a "memory" (i.e., the ability of certain materials to return to an original shape after deformation) for urging the wing portion 21 back to the opened position shown in FIGS. 6 and 8 after the forces thereon are reduced or removed. More specifically, the entire punctal occluder 11 is preferably molded or otherwise constructed as a one-piece, integral unit out of such a material that is soft and flexible in its final state, e.g., a medical grade, physiologically acceptable soft plastic such as silicone or the like. The various edges of the punctal occluder 11 may be rounded to prevent eye irritation, etc. Small fillets may be provided between the distal end 15 of the shank 13 and the distal flange 19, and between the proximal end 17 of the shank 13 and the proximal flange 23 to strengthen the junctions therebetween as will be apparent to those skilled in the art. The punctal occluder of the present invention may be manufactured in various sizes and specific designs to fit a range of typical patients and occlusive requirements. However, the preferred construction and operation of the punctal occluder of the present invention allows three sizes of punctal occluders to fit virtually every punctal size and occlusive requirement. For example, the punctal occluder of the present invention may be manufactured in a small size with a dome or proximal flange diameter of approximately 0.030 inch (0.0762 centimeter), a medium size with a dome or proximal flange diameter of approximately 0.036 inch (0.0914 centimeter), and a large size with a dome or proximal flange diameter of approximately 0.038 inch (0.0965 centimeter).

The method of using the punctal occluder of the present invention to occlude a patient's lacrimal punctum P begins with typical patient examination and evaluation. Assuming a punctal occluder 11 is selected, it is mounted on the distal tip of the insertion tool T by inserting the distal tip of the insertion tool T into the aperture 25 in the proximal flange 23. A punctal dilator (not shown) may be used to dilate the lacrimal punctum P. However, because the unique collapsible distal flange 19 of the punctal occluder 11 presents a diameter when the wing portion 21 is in the first position that is substantially less than the diameter of prior punctal occluders, little or no punctal dilation will be required. In any event, the distal flange 19 and the distal end 15 of the shank 13 are then inserted through the lacrimal punctum P and past the punctal ring R using the insertion tool T as illustrated in FIGS. 6–8. As the wing portion 21 is inserted through the lacrimal punctum P and punctal ring R, the sides of the lacrimal canaliculus C will force it to the first, collapsed position as shown in FIG. 7, thereby reducing the pressure and force required to fully implant the punctal occluder 11. After the distal flange 19 has been thus inserted past the punctal ring R, the wing portion 21 will expand toward the second, opened position as shown in FIG. 8, to fit precisely the lacrimal canaliculus C and resist accidental removal of the punctal occluder 11 from the lacrimal canaliculus C. Since the wing portion 21 will expand to conform to different size lacrimal canaliculus C, size selection errors based on lacrimal canaliculus C diameter and/or punctal ring R thickness, etc., are not as critical as is the case with prior punctal occluders. If it becomes desirable to remove the punctal occluder 11 from the lacrimal canaliculus C after full implantation thereof, the punctal occluder 11 can be grasped under dome or proximal flange 23 with the tips of a pair of forceps F as shown in FIG. 9, and merely lifted up and out of the lacrimal canaliculus C. When such a lifting force is applied to the punctal occluder 11, the wing portion 21 will reverse to the third position as shown in FIG. 9, allowing the distal flange 19 to be easily pulled past the punctal ring R and out the lacrimal punctum P.

As thus constructed and used, the present invention provides a punctal occluder that is biocompatible, soft, non-irritating to tissues, easy to insert, easy to remove, effective, comfortable for the wearer, and secure for "permanent" implantation. In addition, the punctal occluder of the present invention provides a normally conically shaped nose or distal flange that collapses and folds to a relatively small effective diameter to allow it to be easily inserted through the lacrimal punctum P and punctal ring R, that expands and unfolds after it is inserted past the punctal ring R to conform to the size of and occlude the punctal duct or lacrimal canaliculus C, and that reverses and folds to a relatively small effective diameter when force is applied to the punctal occluder to pull it out of the lacrimal punctum P, etc.

Although the present invention has been described and illustrated with respect to a preferred embodiment and a preferred use therefor, it is not to be so limited since modifications and changes can be made therein which are within the full intended scope of the invention.

I claim:

1. A punctal occluder for blocking the flow of lacrimal fluid from the surface of an eye through a lacrimal punctum; said punctal occluder comprising:

(a) a shank having a distal end for insertion into the lacrimal punctum and having a proximal end;

(b) a proximal flange attached to said proximal end of said shank, said proximal flange being formed of a dimension to prevent complete migration of said punctal occluder into the lacrimal punctum and to prevent said punctal occluder from passing through the lacrimal punctum; and (c) a distal flange attached to said distal end of said shank for insertion into the lacrimal punctum; said distal flange including a wing portion having a collapsed position for allowing easy insertion of said distal flange into the lacrimal punctum, having an opened position for hindering unintentional removal of said distal flange from the lacrimal punctum, and having a reversed position for allowing easy removal of said distal flange from the lacrimal punctum; said wing portion having a first end and a second end; said first end of said wing portion being attached to said shank; said second end of said wing portion being located closer to said proximal flange than said first end of said wing portion when said wing portion is in said collapsed or opened positions; said second end of said wing portion being located farther from said proximal flange than said first end of said wing portion when said wing portion is in said reversed position.

2. The punctal occluder of claim 1 in which said wing portion of said distal flange has a reversed position for allowing easy removal of said distal flange from the lacrimal punctum.

3. The punctal occluder of claim 1 in which said wing portion of said distal flange is normally urged to said opened position.

4. The punctal occluder of claim 1 in which said wing portion of said distal flange is constructed out of a material that is soft and flexible in its final state for allowing movement thereof from said opened position to said collapsed position when force is directed inwardly on said wing portion, and from said opened position to said reversed position when force is directed on said wing portion in a direction toward said distal end of said shank; said material having memory for urging said wing portion back to said opened position after the force thereon is reduced.

5. The punctal occluder of claim 1 in which said shank includes a proximal end, and in which is included a proximal flange attached to said proximal end of said shank for preventing complete migration of said punctal occluder into the lacrimal punctum.

6. The punctal occluder of claim 1 in which the transverse width of said punctal occluder taken through said wing portion with said wing portion in said collapsed position is less than 75% of the transverse width of said punctal occluder taken through said wing portion with said wing portion in said opened position; and in which the transverse width of said punctal occluder taken through said wing portion with said wing portion in said reversed position is less than 75% of the transverse width of said punctal occluder taken through said wing portion with said wing portion in said opened position.

* * * * *